(12) United States Patent
Tekulve (10) Patent No.: US 8,282,648 B2
(45) Date of Patent: Oct. 9, 2012

(54) BONE CEMENT NEEDLE

(75) Inventor: Kurt J. Tekulve, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1328 days.

(21) Appl. No.: 11/960,356

(22) Filed: Dec. 19, 2007

(65) Prior Publication Data

US 2009/0163872 A1 Jun. 25, 2009

(51) Int. Cl.
*A61M 5/178* (2006.01)
*A61M 5/00* (2006.01)
*A61B 17/58* (2006.01)

(52) U.S. Cl. ..................... 606/92; 604/164.11

(58) Field of Classification Search ............ 604/164.11; 606/79–85, 86 R, 92–95
See application file for complete search history.

(56) References Cited

U.S. PATENT DOCUMENTS

| | | | |
|---|---|---|---|
| 3,112,743 A | 12/1963 | Cochran et al. | |
| 4,466,435 A | 8/1984 | Murray | |
| 4,625,722 A * | 12/1986 | Murray | 606/95 |
| 5,108,403 A | 4/1992 | Stern | |
| 5,620,456 A * | 4/1997 | Sauer et al. | 606/185 |
| 5,752,970 A * | 5/1998 | Yoon | 606/185 |
| 6,325,812 B1 * | 12/2001 | Dubrul et al. | 606/185 |
| 6,425,887 B1 * | 7/2002 | McGuckin et al. | 604/272 |
| 6,436,119 B1 * | 8/2002 | Erb et al. | 606/198 |
| 6,524,319 B1 * | 2/2003 | Schmidt et al. | 606/86 R |
| 6,592,559 B1 | 7/2003 | Pakter et al. | |
| 6,676,665 B2 * | 1/2004 | Foley et al. | 606/105 |
| 6,719,746 B2 * | 4/2004 | Blanco | 604/506 |
| 6,730,095 B2 | 5/2004 | Olson, Jr. et al. | |
| 6,733,472 B1 | 5/2004 | Epstein et al. | |
| 6,863,672 B2 * | 3/2005 | Reiley et al. | 606/79 |
| 6,875,219 B2 * | 4/2005 | Arramon et al. | 606/92 |
| 7,905,884 B2 * | 3/2011 | Simonton et al. | 606/79 |
| 2005/0033303 A1 * | 2/2005 | Chappuis et al. | 606/80 |
| 2005/0182417 A1 * | 8/2005 | Pagano | 606/92 |
| 2005/0261781 A1 | 11/2005 | Sennett et al. | |
| 2006/0195115 A1 | 8/2006 | Ferree | |
| 2007/0067043 A1 | 3/2007 | Dericks | |
| 2007/0142842 A1 | 6/2007 | Krueger et al. | |
| 2007/0255281 A1 * | 11/2007 | Simonton et al. | 606/60 |

* cited by examiner

*Primary Examiner* — Kevin T Truong
*Assistant Examiner* — Christopher Beccia
(74) *Attorney, Agent, or Firm* — Woodard, Emhardt, Moriarty, McNett & Henry LLP

(57) ABSTRACT

A needle assembly for dispensing a bone cement mixture is provided. The needle assembly includes a cannula defining an inner lumen, the cannula having an outlet end for dispensing the bone cement mixture from the assembly. The outlet end has at least one tip moveable between an expanded position and a collapsed position. The tip is configured to cut the bone cement mixture in the collapsed position when the cannula is rotated. The needle assembly also has an inner member disposed within the inner lumen of the cannula, which is movable between an extended position and a retracted position. The inner member is operable to hold the tip in the expanded position when the inner member is in the extended position. The tip automatically collapses into the collapsed position when the inner member is in the retracted position. A method of introducing a bone cement mixture into a damaged bone of a patient is also disclosed.

22 Claims, 5 Drawing Sheets

BONE CEMENT NEEDLE

BACKGROUND OF THE INVENTION

1. Field of the Invention

The present invention relates to medical devices and more particularly, to needles for insertion of a bone cement mixture into a cavity of a damage bone.

2. Background

There is a clinical need to fill and stabilize damaged bones of patients, such as for example, filling defects in collapsed vertebrae of patients suffering from severe back pain caused by osteoporosis, metastatic tumors or back injuries. Currently, these defects are repaired using multi-component bone cements that are injected into the damaged bone where the mixture chemically reacts or cures to form a solid support structure. The most widely used bone cements are based on polymethylmethacrylate (PMMA) and hydroxyapatite.

One procedure that is typically used to fill defects in collapsed vertebrae is known as vertebroplasty. This procedure involves injecting bone cement directly into the fracture void through a minimally invasive cannula or needle. The bone cement may be radio-opaque and monitored via fluoroscopy. The cement may be pressurized by a syringe to cause the cement to fill the void. Once cured, the cement stabilizes the vertebra and reduces pain. Kyphoplasty is another similar procedure that may be used to inject bone cement into a fracture void. Typically, thicker bone cements are used with kyphoplasty than with vertebroplasty.

Although safe and effective, one issue with vertebroplasty and kyphoplasty is containment of the bone cement within the area of the vertebra having the defect. Cement may typically flow beyond the confines of the bone into other areas of the body. Typically, the bone cement has a high level of coherence such that the cement particles tend to adhere to other surrounding cement particles. Therefore, when an application cannula is withdrawn from the body, it will carry a trail of bone cement with it, which is typically cut near the skin surface.

To address the problem of cement containment within the bone fracture or void area, some practitioners have utilized fillable mesh bags or containers inside of the vertebra. However, upon filling, the expansion of such a bag or container can cause undesirable compaction on the surrounding fractured bone. Furthermore, the bag or container may still be permeable and release some of the bone cement into the surrounding body cavity. Another drawback of using mesh bags and/or containers is that they may add an expense to the procedure.

In view of the above and other defects known in the art, there remains a need for a bone cement delivery system that more adequately effects bone cement containment within the vertebra fracture, without adding significant costs to the procedure.

BRIEF SUMMARY OF THE INVENTION

The present invention provides an affordable, effective bone cement delivery system that cuts or shears viscous bone cement at the fracture area, thereby decreasing the likelihood of bone cement being applied in other areas of the body cavity.

In one aspect of the present invention, a needle assembly for dispensing a bone cement mixture is provided. The needle assembly includes a cannula defining an inner lumen, the cannula having an outlet end for dispensing the bone cement mixture from the assembly. The outlet end has one or more tips moveable between an expanded position and a collapsed position. The tip or tips are configured to cut the bone cement mixture in the collapsed position when the cannula is rotated. The needle assembly also has an inner member disposed within the inner lumen of the cannula. The inner member is movable between an extended position and a retracted position and is operable to hold the tip or tips in the expanded position when the inner member is in the extended position. The tip or tips automatically collapse into the collapsed position when the inner member is in the retracted position.

In another aspect, a cannula for dispensing a bone cement mixture into a damaged bone of a patient is provided. The cannula has a tubular body having an inner side defining an inner lumen. The cannula has an inner diameter and an outlet end for dispensing the bone cement mixture from the cannula. The cannula also has a plurality of tips connected to the outlet end, which are movable between an expanded position and a collapsed position. The plurality of tips extends across the inner diameter in the collapsed position and defines a plurality of openings at the outlet end. The plurality of tips is configured to cut the bone cement mixture in the collapsed position when the needle cannula is rotated.

In yet another aspect, a method of introducing a bone cement mixture into a damaged bone of a patient is provided. The method includes a step of piercing the damaged bone of the patient with a needle assembly to define a bone opening. The needle assembly is provided having a cannula and an inner member movable to extend from an outlet end of the cannula. The cannula has an inner side defining an inner lumen and has an inner diameter. A plurality of tips is connected to the outlet end, the tips being movable between an expanded position and a collapsed position. The inner member is operable to hold the plurality of tips in the expanded position when the inner member extends from the cannula. The method includes a step of advancing the bone cement mixture through the lumen of the cannula and dispensing the bone cement mixture into the bone opening. Another step includes filling the damaged bone of the patient with the bone cement mixture. The method includes a step of retracting the inner member into the lumen of the cannula, the plurality of tips automatically collapsing into the collapsed position when the inner member is retracted into the lumen of the cannula. In the collapsed position, the plurality of tips extends across the inner diameter and defines a plurality of openings at the outlet end. The method also includes rotating the cannula when the plurality of tips is in the collapsed position, the plurality of tips cutting the bone cement mixture upon rotation of the cannula.

Further objects, features and advantages of the invention will become apparent from consideration of the following description and the appended claims when taken in connection with the accompanying drawings.

DETAILED DESCRIPTION OF THE INVENTION

Figure 1:
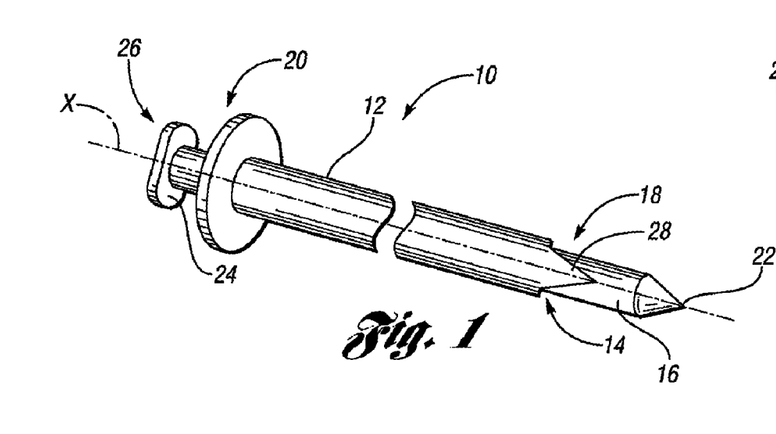
FIG. 1 is a perspective view of a needle assembly having a cannula and an inner member, in accordance with the principles of the present invention.

With reference to FIG. 1, a needle assembly for dispensing a bone cement mixture is illustrated and generally designated at 10. The needle assembly 10 includes a cylindrical cannula 12 defining an inner lumen 14 through the center of the cannula 12 along a center longitudinal axis X of the cannula 12. A cylindrical inner member 16 is disposed within the lumen 16 of the cannula 12. The cannula 12 has an outlet end 18 for dispensing the bone cement mixture from the assembly 10. The cannula 12 also has an inlet end 20 for receiving the bone cement mixture, which will be described in further detail below.

The inner member 16 may be slid or otherwise moved within the lumen 16 of the cannula 12 between an extended position and a retracted position. In FIG. 1, the inner member 16 is shown in the extended position, wherein the inner member 16 extends from the outlet end 18 of the cannula 12. The inner member 16 may be a needle stylet, as shown in FIG. 1, or it may have any other suitable configuration, for example, the inner member 16 could be an inner cannula. The stylet 16 has a pointed end 22 for piercing through a damaged bone.

The stylet 16 may have a handle 24 at a proximal end 26 for gripping by the user to move the stylet 16 within the lumen 14 and to remove the stylet 16 from the cannula 12.

The inner member 16 may be formed of a flexible, high-tensile strength polymeric material, such as polyetheretherketone (PEEK), or any other suitable material, such as metal or other polymers.

The outlet end 18 of the cannula 12 has a pair of tips 28 (in FIG. 1, only one of the pair of tips 28 may be seen, as the other is hidden behind the inner member 16). The tips 28 may each have a spring force such that each tip 28 tends to automatically collapse toward the center longitudinal axis X of the cannula 12. Thus, the tips 28 are moveable between an expanded position and a collapsed position.

The tips 28 are preferably formed of a superelastic material, such as nickel titanium (Nitinol®). More preferably, the tips 28 are formed unitarily with the cannula 12, which is also formed of nickel titanium. In the alternative, the tips 28 may be formed of a material different than the material of the cannula 12, and the tips 28 may be attached to, rather than formed unitarily with, the cannula 12. Furthermore, the tips 28 and/or the cannula 12 could alternatively be formed of another superelastic material, such as stainless steel, cobalt-chromium-nickel-molybdenum-iron alloy, or cobalt-chrome alloy by way of example. It should be understood that the tips 28 may be formed of any suitable material that will result in the tips 28 being self-collapsing, such as shape memory material.

Shape memory materials or alloys have the desirable property of becoming rigid, i.e., returning to a remembered state, when heated above a transition temperature. A shape memory alloy suitable for the present invention is nickel titanium. This material may be formed such that when it is heated above the transition temperature, the material undergoes a phase transformation from martensite to austenite, such that material returns to its remembered state. The transition temperature is dependent on the relative proportions of the alloying elements nickel and titanium and the optional inclusion of alloying additives.

In one embodiment, the tips 28 are made from Nitinol with a transition temperature that is slightly below normal body temperature of humans, which is about 98.6° F. Thus, when the tips 28 are inserted into a bone opening and exposed to normal body temperature, the alloy of the tips 28 will transform to austenite, that is, the remembered state, which for one embodiment of the present invention is the collapsed state.

In another embodiment, the tips 28 are made from Nitinol with a transition temperature that is above normal body temperature of humans, which is about 98.6° F. Thus, when the tips 28 are inserted into a bone opening and exposed to normal body temperature, the tips 28 are in the martensitic state so that the tips 28 are sufficiently ductile to bend or form into a desired shape, which for the present invention is the expanded state. The tips 28 may then be heated to transform the alloy to austenite so that it becomes rigid and returns to a remembered state, which for the tips 28 is the collapsed state.

In the expanded position, the tips 28 extend from the cannula 12 in a substantially straight line along the exterior of the cannula 12. In the alternative, the tips 28 could extend slightly inward toward the center longitudinal axis X in the expanded position. The inner member 16 is operable to hold each tip 28 in the expanded position when the inner member 16 is in the extended position, as shown in FIG. 1. In other words, the inner member 16 is operable to straighten the tips 28.

Figure 2:
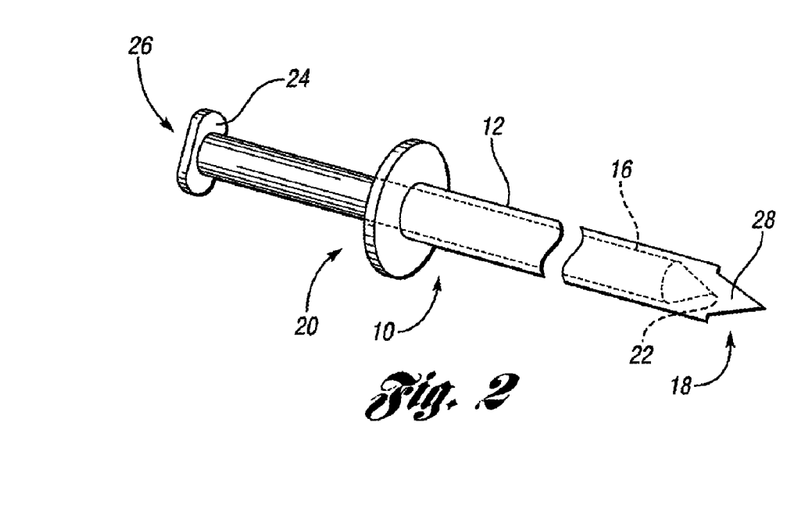
FIG. 2 is a perspective view of the needle assembly of FIG. 1, having the inner member removed from the cannula, according to the principles of the present invention.
Figure 3:
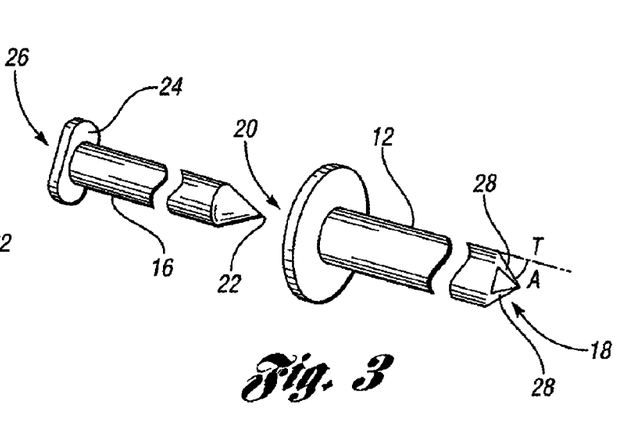
FIG. 3 is a perspective side view of the cannula of FIGS. 1 and 2, in accordance with the principles of the present invention.
Figure 4:
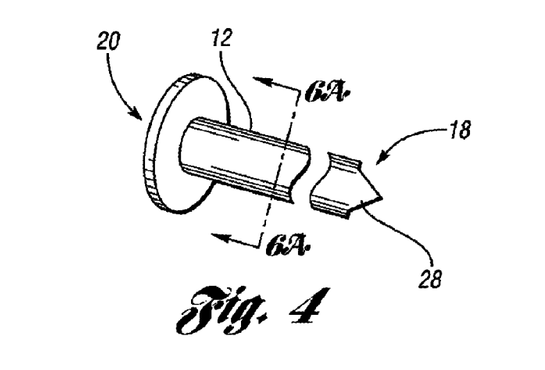
FIG. 4 is a perspective front view of the cannula of FIGS. 1-3, the cannula being rotated 90-degrees from the view of FIG. 3, in accordance with the principles of the present invention.

With reference to FIGS. 2-4, the stylet 16 is shown removed from the cannula 12. After the stylet 16 is moved completely into the cannula 12 in the retracted position, the tips 28 will automatically collapse inward toward the center longitudinal axis X, by virtue of the spring force contained in the tips 28, or by virtue of heating or cooling of the shape memory material, as described above. In other words, the tips 28 return to their preset shape. FIG. 2 shows the stylet immediately after being pulled into the retracted position, and for clarity the tips 28 are shown in the expanded position, although in reality, they will automatically collapse immediately after the stylet 16 is retracted into the lumen 14 of the cannula 12. With reference to FIGS. 3 and 4, the tips 28 are shown in a side view (FIG. 3) and a front view (FIG. 4), wherein the tips 28 have collapsed into the collapsed position, toward the center longitudinal axis of the cannula 12.

Figure 5:
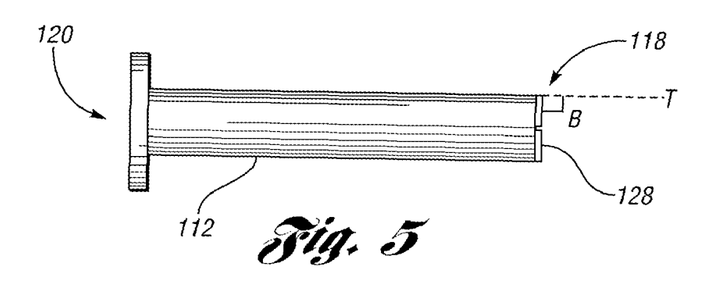
FIG. 5 is a side view of another cannula according to the principles of the present invention.

In FIG. 3, it may be seen that the tips 28 collapse inward at approximately a 45-degree angle A with respect to a tangent line T extending from the main body of the cannula 12 in the collapsed position. In the alternative, the tips 28 could collapse inward at any other suitable angle, for example, forming a 60-degree angle (not shown) with the tangent line T extending from the main body of the cannula in the collapsed position. As another example, with reference to FIG. 5, the tips 128 may collapse inward to form a 90-degree angle B with respect to a tangent line T of the cannula 12 in the collapsed position.

Figure 6A:
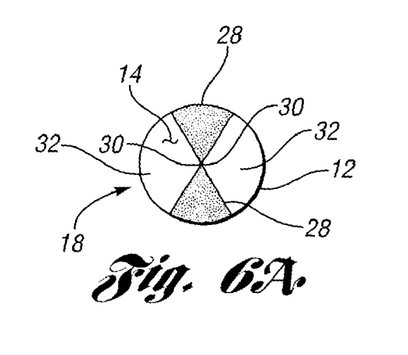
FIG. 6A is an end view of the cannula of FIGS. 1-4, in accordance with the principles of the present invention.

With reference to FIGS. 6A-6D, end views are illustrated of various embodiments for tips 28, 228, 328, 428 of the cannula 12, 212, 312, 412. For example, FIG. 6A shows a pair of tips 28 in the collapsed position as hereinbefore discussed with reference to FIGS. 1-4. Each tip 28 of the pair of tips 28 has a pointed end 30 that extends across a portion of the diameter of the lumen 14 of the cannula 12 to contact the pointed end 30 of each other tip 28 of the pair of tips 28. Thus, in the collapsed position, the tips 28 contact each other to define a plurality of openings 32 at the outlet end 18 of the cannula 12 in the collapsed position. In this embodiment, each tip 28 has a triangular shape, wherein one side of each tip 28 is connected to the main body portion of the cannula 12.

Figure 6B:
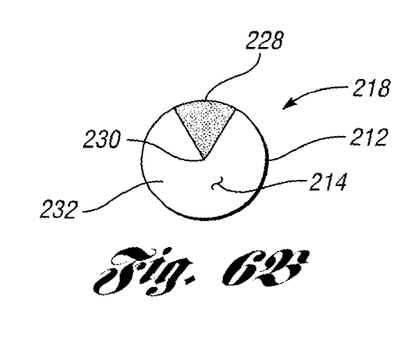
FIG. 6B is an end view of yet another cannula, according to the principles of the present invention.

With reference to FIG. 6B, a single tip 228 is connected to the outlet end 218 of a cannula 212. In all other respects, the cannula 212 and inner member (not shown in FIG. 6B) may be similar to those hereinbefore or hereinafter described. Like the tips 28 of FIGS. 1-4 and 6A, the tip 228 of FIG. 6B is also configured to move between an expanded position and a collapsed position, the tip 228 having a spring force such that the tip 228 automatically collapses into the collapsed position shown upon removal of the inner member (not shown). In the alternative, the tip 228 may automatically collapse upon heating or cooling the shape memory material, as described above. The single tip 228 may have a triangular shape as shown. One opening 232 surrounds the tip 228.

Figure 6C:
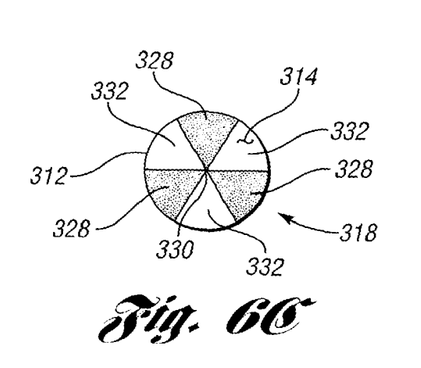
FIG. 6C is an end view of still another cannula, according to the principles of the present invention.

With reference to FIG. 6C, a triad of tips 328 is connected to the outlet end 318 of the cannula 312. In all other respects, the cannula 312 and the inner member (not shown in FIG. 6C) may be similar to those hereinbefore or hereinafter described. Like the tips 28, 128, 228 of the previous FIGS. 1-6B, the tips 328 of FIG. 6C are also configured to move between an expanded position and a collapsed position. The tips 328 have a spring force such that the tips 328 automatically collapse into the collapsed position shown upon removal of the inner member (not shown). In the alternative, the tips 328 may automatically collapse upon heating or cooling the shape memory material as described above. The tips 328 may have a triangular shape as shown. The tips 328 each extend partially across the diameter of the lumen 314 of the cannula 312 to contact each other and define a plurality of openings 332 through which bone cement may be dispensed.

Figure 6D:
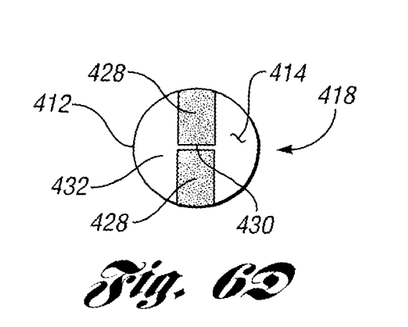
FIG. 6D is an end view of still another cannula, according to the principles of the present invention.
Figure 7:
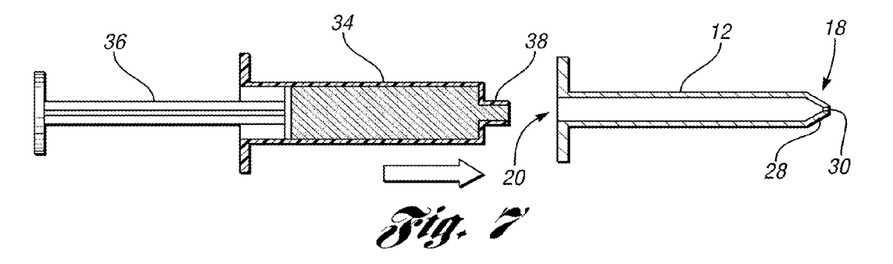
FIG. 7 is a cross-sectional view of the cannula of FIGS. 1-4 and a syringe, according to the principles of the present invention.
Figure 8:
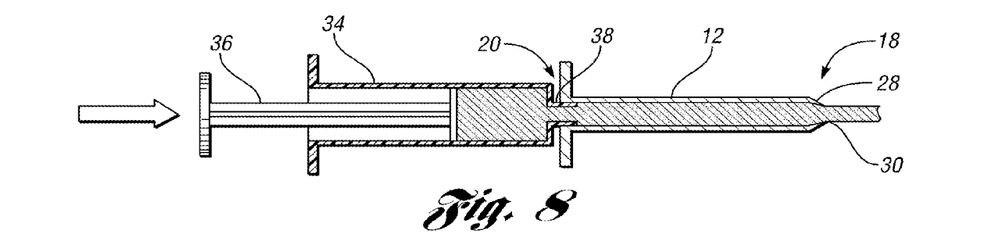
FIG. 8 is a cross-sectional view of the cannula mated to the syringe of FIG. 7 with bone cement being dispensed from the cannula, according to the principles of the present invention.

With reference to FIG. 6D, a pair of tips 428 is connected to the outlet end 418 of the cannula 412. In all other respects, the cannula 412 and the inner member (not shown in FIG. 6D) may be similar to those hereinbefore or hereinafter described. Like the tips 28, 128, 228, 328 of the previous FIGS. 1-6C, the tips 428 of FIG. 6D are also configured to move between an expanded position and a collapsed position. The tips 428 may have a spring force such that the tips 428 automatically collapse into the collapsed position shown upon removal of the inner member (not shown). In the alternative, the tips 428 may automatically collapse upon heating or cooling the shape memory material, as described above. The tips 428 differ from the tips 28, 228, 328 hereinbefore described as they do not have a triangular shape; the tips 428 have a rectangular shape with one side of the rectangle being connected to the main body of the cannula 412. It is preferable, but not mandatory, that the tips 428 each extend partially across the diameter of the lumen 414 of the cannula 412 to contact each other and define a plurality of openings 432 through which bone cement may extend.

In any of the embodiments of tips 28, 128, 228, 328, 428 described herein, each of the tips 28, 128, 228, 328, 428 have side edges that are configured to shear or cut the bone cement mixture being dispensed therefrom, which be described in further detail below, when the tips 28, 128, 228, 328, 428 are in the collapsed position.

With reference to FIGS. 7-11, after the needle assembly 10 has been inserted into a bone cavity, the stylet 16 may be removed, while the cannula 12 is left within the bone cavity. Although the bone cavity is not illustrated herein, it should be understood that in each of FIGS. 2-11, the cannula 12 is left in the bone cavity. A syringe 34 having a pusher rod 36 is filled with a bone cement mixture, which may be mixed in the syringe 34 itself or separately from the syringe 34. A tip 38 of the syringe is matingly connected to the lumen 14 of the cannula 12. The pusher rod 36 is used to push the bone cement mixture into the lumen 14 of the cannula 12, and further, to dispense the bone cement mixture from the outlet end 18 of the cannula 12 and into the bone cavity (or other suitable delivery site).

The bone cement mixture may be radio-opaque such that the filling of the bone cavity may be monitored via fluoroscopy, and/or the bone cement mixture may be made of any suitable material, as is known to those having ordinary skill in the art. It is contemplated that the present invention will be particularly useful with bone cements having at least a moderate level of viscosity that would be dragged by the application cannula absent some shearing force cutting the bone cement.

Figure 9:
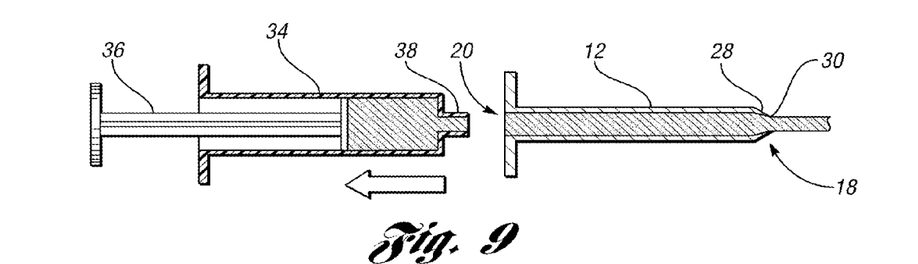
FIG. 9 is a cross-sectional view of the cannula and syringe of FIGS. 7 and 8, the syringe being removed from the cannula and bone cement extending from the outlet end of the cannula, in accordance with the principles of the present invention.
Figure 10:
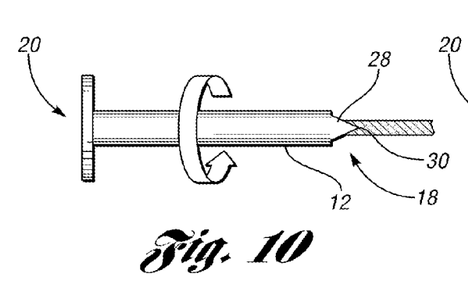
FIG. 10 is a side view of the cannula of FIGS. 7-9, the cannula being rotated to cut the bone cement extending therefrom, in accordance with the principles of the present invention.
Figure 11:
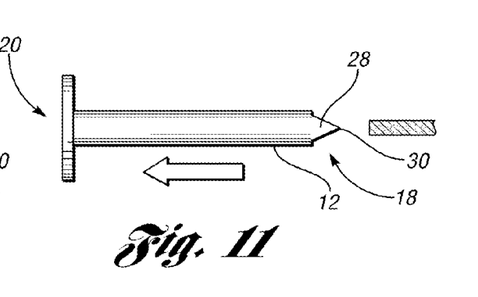
FIG. 11 is a side view of the cannula of FIGS. 7-10, the cannula being removed from the bone cement application area, the applied bone cement being detached from the cannula, according to the principles of the present invention.

When the practitioner desires to stop the filling process and remove the cannula 12 from the bone cavity, the practitioner may first remove the syringe 34 from the cannula 12 as shown in FIG. 9. Thereafter, the cannula 12 may be rotated. The edges of the tips 28 are provided with sufficient sharpness to cut the bone cement mixture upon rotation of the cannula 12 when the tips 28 are in the collapsed state. A suction force may then be used, if desired, to extract excess bone cement from the cannula to avoid further application of the bone cement within the body. With the bone cement being severed at the bone cavity area, or other delivery site, the bone cement may be applied in only the desired areas, without dragging bone cement through the body to the surface of the skin to be cut.

Figure 12A:
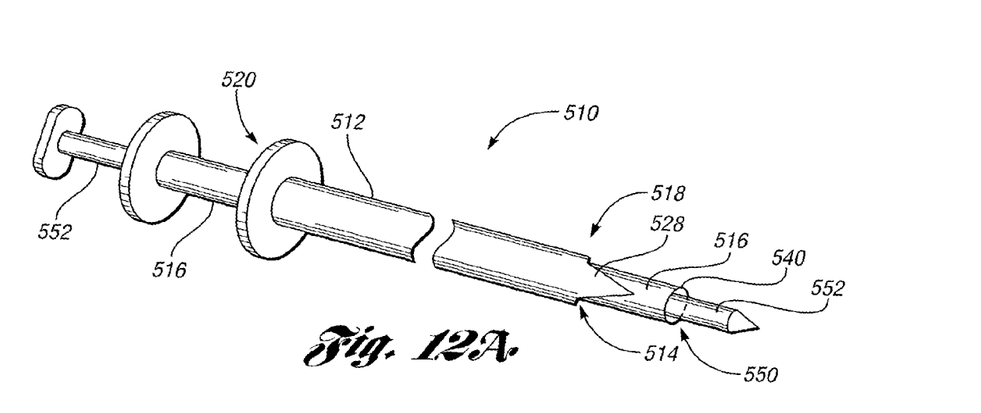
FIG. 12A is a perspective view of still another needle assembly, according to the principles of the present invention, the needle assembly having an inner cannula and a stylet extending from an outlet end of an outer cannula.
Figure 12B:
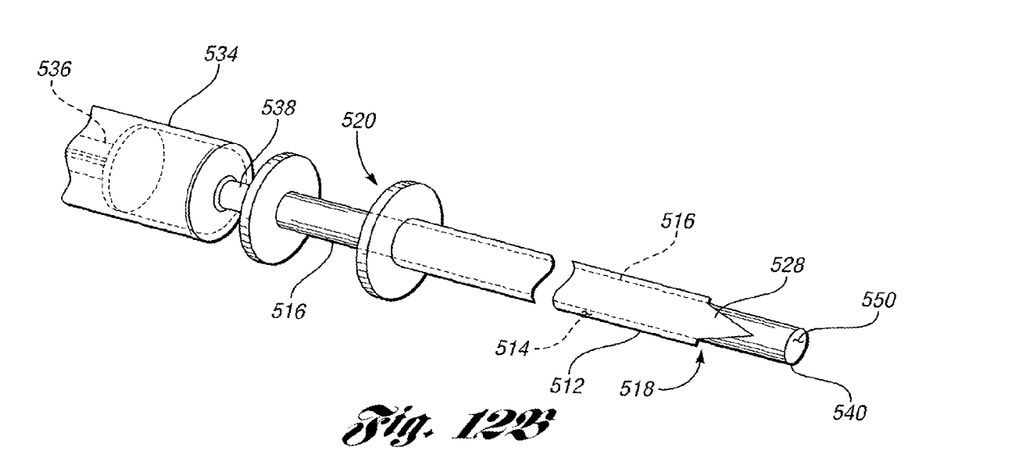
FIG. 12B is a perspective view of the needle assembly of FIG. 12A, with the stylet removed and the inner cannula in communication with a syringe, in accordance with the principles of the present invention.
Figure 12C:
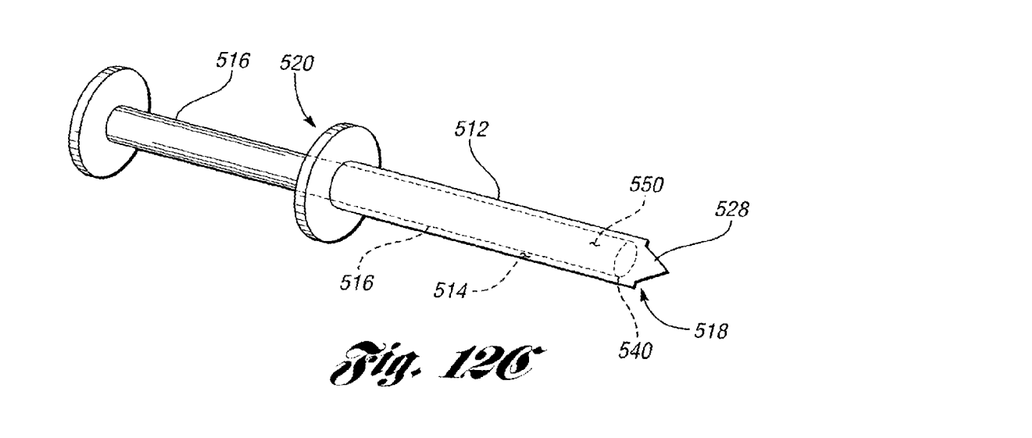
FIG. 12C is a perspective view of the needle assembly of FIGS. 12A-12B, the inner cannula being retracted into the outer cannula, in accordance with the principles of the present invention.

With reference to FIGS. 12A-12C, another needle assembly 510 is illustrated. The needle assembly 510 of FIG. 12A-12C has an outer cannula 512, which is substantially similar to one of the cannulas 12, 112, 212, 312, 412 of the previous figures. As such, the outer cannula 512 defines an inner lumen 514 and has an inlet end 520, an outlet end 518, at least one tip 528, and an inner member 516 disposed within the lumen 514 of the outer cannula 512. In FIGS. 12A-12C, the inner member The inner cannula 516 may be positioned in the extended position to deliver an unimpeded flow of bone cement mixture into the bone opening. Thus, the inner cannula 516 defines a lumen 550 therein through which the bone cement mixture is advanced. A stylet 552 may be inserted through the lumen 550 of the inner cannula 516 to pierce the damaged bone. Before delivering the bone cement mixture, the stylet 552 is then removed from the inner cannula 516. In the alternative, the inner cannula 516 could have a sharp distal end 540 to pierce through the damage bone.

After the bone opening is filled with bone cement mixture, the inner cannula 516 may be retracted into the outer cannula 512, allowing the tips 528 to automatically collapse in the collapsed position. The outer cannula 512 may then be rotated to cut the bone cement mixture. Thus, in the embodiment of FIGS. 12A-12C, the bone cement mixture is delivered into the bone opening while the tips 528 are held in the open position, which may be ideal for very viscous bone cement mixtures in which the tips 528 may impede the flow of the bone mixture to an undesirable level.

With reference to FIG. 12A, the inner cannula 516 extends from the outlet end 518 of the outer cannula 512, thereby straightening the tips 528 in the expanded position. The stylet 552 extends from the distal end 540 of the inner cannula 516 to pierce the damaged bone. With reference to FIG. 12B, the stylet 552 has been removed from the needle assembly 510. To apply the bone cement mixture, the tip 538 of a syringe 534 having a plunger 536 is placed in fluid communication with the lumen 550 of the inner cannula 516. The plunger 536 of the syringe 534 is operable to advance bone cement into the inner cannula 516 and further into a bone opening, provided that the needle assembly 510 is located in the bone opening when the bone cement mixture is being advanced out of distal end 540 of the inner catheter 516.

After applying the bone cement mixture, the inner cannula 516 may be retracted into the outer cannula 512 in the retracted position, as shown in FIG. 12C. When the inner cannula 516 is retracted into the lumen 514 of the cannula 512, the tips 428 automatically collapse into the collapsed position, such that the bone cement mixture may be cut by rotating the outer cannula 512. For a representative end view of the tips 528 in the collapsed position, see FIGS. 6A-6D, as any one of these configurations or others could be used.

In the alternative, the inner cannula 516 may be removed from the outer cannula 512 before the bone cement mixture is applied, and the bone cement mixture may be applied directly into the lumen 514 of the outer cannula 512, similarly to the embodiments of FIGS. 7-11.

Figure 13:
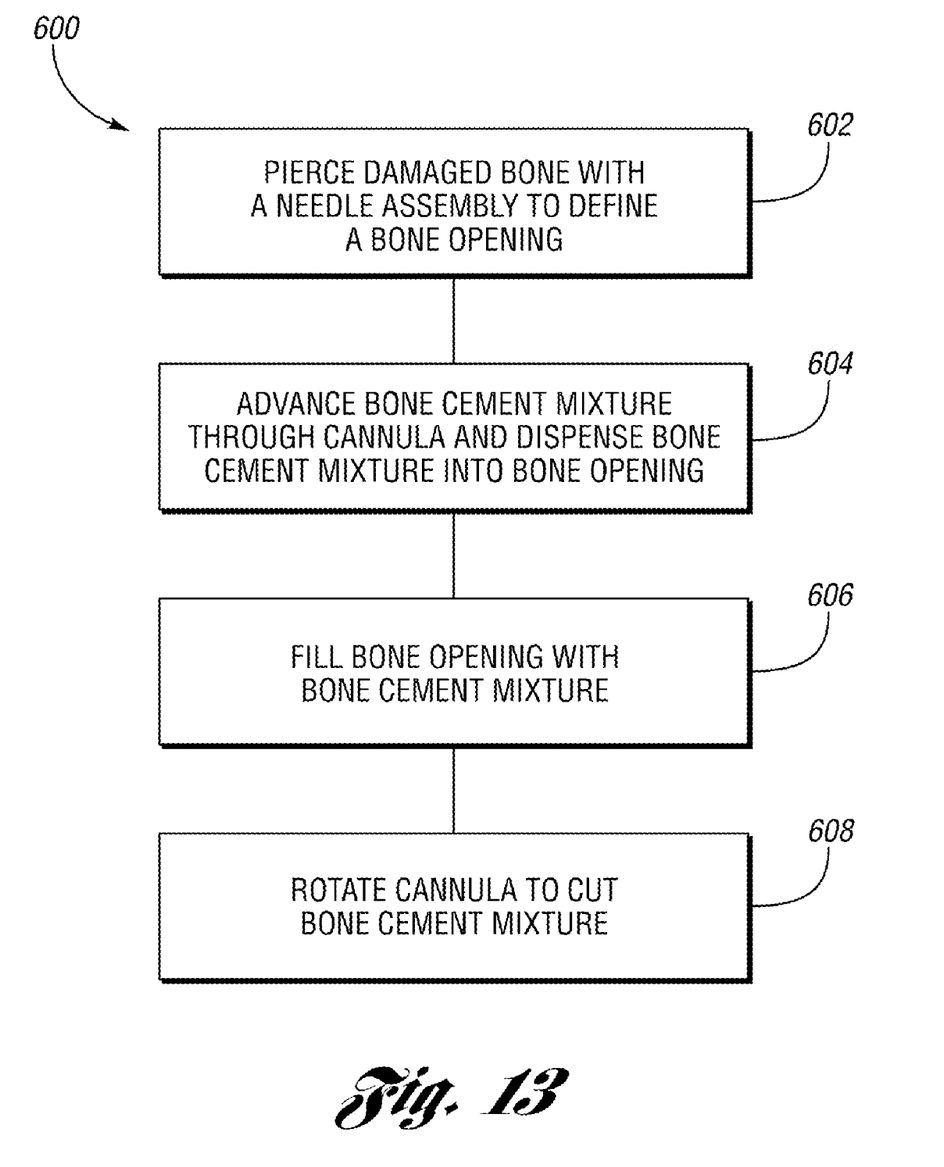
FIG. 13 is a block diagram illustrating a method of introducing a bone cement mixture into a damaged bone of a patient, according to the principles of the present invention.

With reference to the block diagram of FIG. 13, a method of introducing a bone cement mixture into a damaged bone of a patient is illustrated and generally designated at 600. For illustration of the devices used for the method 600, reference may be made to FIGS. 7-12C. The method 600 includes a step 602 of piercing the damaged bone of the patient with a needle assembly to define a bone opening. The needle assembly is preferably one of the types hereinbefore described. As such, the needle assembly has a cannula and an inner member movable to extend therefrom. The cannula has an inner side defining an inner lumen and has an inner diameter and an outlet end. A plurality of tips is connected to the outlet end. The tips are movable between an expanded position and a collapsed position. The inner member is operable to hold the plurality of tips in the expanded position when the inner member extends from the cannula in an extended position.

The inner member could be, for example, a stylet or an inner cannula, as hereinbefore described. If the inner member is a stylet, it is retracted into the cannula and removed from the cannula. If the inner member is an inner cannula, the inner member may extend from the outlet end of the cannula to deliver bone cement mixture, and then be retracted into the lumen of the cannula. When the inner member is retracted into the cannula, the plurality of tips automatically collapses into the collapsed position, as hereinbefore described. In the collapsed position, the plurality of tips extends across the inner diameter to define a plurality of openings at the outlet end of the cannula.

To apply bone cement mixture, fluid communication between the lumen of the cannula and an injection device comprising the bone cement mixture is provided. If the inner member is an inner cannula, the fluid communication is provided between the lumen of the inner cannula and the injection device. The bone cement mixture is dispensed into the lumen of the cannula, and the method 600 includes a step 604 of advancing the bone cement mixture through the lumen of the cannula and dispensing the bone cement mixture into the bone opening. The method 600 further includes a step 606 of filling the bone opening with the bone cement mixture.

Thereafter, the practitioner should cease advancing the bone cement mixture through the lumen of the cannula. The method 600 then includes a step 608 of rotating the cannula when the plurality of tips are in the collapsed position, the plurality of tips cutting the bone cement mixture upon rotation of the cannula. This step 608 may also include completely separating the bone mixture into a first portion of the bone cement mixture located in the cannula and a second portion of the bone cement mixture located in the damaged bone, which allows removal of the cannula without dragging the bone cement mixture through the body cavity to the skin level. The cannula may then be retracted from the damaged bone.

As a person skilled in the art will readily appreciate, the above description is meant as an illustration of the implementation of the principles of this invention. This description is not intended to limit the scope or application of this invention in that the invention is susceptible to modification variation and change, without departing from the spirit of this invention, as defined in the following claims.

The invention claimed is:

1. A needle assembly for dispensing a bone cement mixture, the needle assembly comprising:
   a cannula having an inner lumen defined therethrough, the cannula having an outlet end for dispensing the bone cement mixture from the assembly, the outlet end having at least one tip moveable between an expanded position and a collapsed position, the at least one tip being configured to cut the bone cement mixture in the collapsed position when the cannula is rotated; and
   an inner member disposed within the inner lumen of the cannula and being movable between an extended position and a retracted position, the inner member operable to hold the at least one tip in the expanded position when the inner member is in the extended position, the at least one tip configured to automatically collapse to the collapsed position when the inner member is in the retracted position.

2. The needle assembly of claim 1, wherein the at least one tip is a plurality of tips.

3. The needle assembly of claim 1, wherein the at least one tip is formed of a superelastic material.

4. The needle assembly of claim 3, wherein the superelastic material is nickel titanium.

5. The needle assembly of claim 4, wherein the cannula is formed of nickel titanium, the cannula being unitarily formed with the at least one tip.

6. The needle assembly of claim 2, wherein each tip of the plurality of tips has a pointed end.

7. The needle assembly of claim 6, wherein the plurality of tips contact each other at the pointed ends in the collapsed position.

8. The needle assembly of claim 7, wherein the cannula has an inner diameter, the plurality of tips extending across the inner diameter in the collapsed position.

9. The needle assembly of claim 8, wherein the plurality of tips defines a plurality of openings at the outlet end of the cannula in the collapsed position.

10. The needle assembly of claim 7, wherein each tip of the plurality of tips has a triangular shape including three sides, wherein one side of each tip of the plurality of tips is connected to a body portion of the cannula, and the other sides of each tip are free from being connected to any part.

11. The needle assembly of claim 1, wherein the inner member is a stylet that extends from the outlet end of the cannula in the extended position to pierce through a damaged bone.

12. The needle assembly of claim 11, wherein the stylet is retracted into the lumen of the cannula in the retracted position, the at least one tip being configured with a spring force to automatically collapse into the collapsed position when the stylet is retracted into the lumen of the cannula.

13. The needle assembly of claim 1, wherein the cannula is an outer cannula and the inner member is an inner cannula operable to deliver the bone cement mixture to a target area, the inner cannula extending from the outlet end of the outer cannula in the extended position and being retracted into the lumen of the outer cannula in the retracted position.

14. The needle assembly of claim 13, wherein the at least one tip is configured with a spring force to automatically collapse into the collapsed position when the inner cannula is retracted into the lumen of the outer cannula.

15. A cannula for dispensing a bone cement mixture into a damaged bone of a patient, the cannula comprising:
a tubular body having an inner side defining an inner lumen and having an inner diameter, the tubular body having an outlet end for dispensing the bone cement mixture from the needle cannula; and
a plurality of tips connected to the outlet end, the plurality of tips movable between an expanded position and a collapsed position, the plurality of tips extending across the inner diameter in the collapsed position and defining a plurality of openings at the outlet end, the plurality of tips being configured to cut the bone cement mixture in the collapsed position when the cannula is rotated.

16. The cannula of claim 15, wherein the plurality of tips is formed of a superelastic material.

17. The cannula of claim 16, wherein the cannula is formed of nickel titanium, the tubular body being unitarily formed with the plurality of tips.

18. The cannula of claim 15, wherein each tip of the plurality of tips has a pointed end.

19. The cannula of claim 18, wherein the plurality of tips contact each other at the pointed ends in the collapsed position.

20. The needle assembly of claim 1, wherein in the extended position a portion of the inner member extends from the cannula along a central longitudinal axis of the cannula.

21. The needle assembly of claim 1, wherein in the collapsed position the at least one tip is oriented toward a central longitudinal axis of the cannula.

22. The needle assembly of claim 6, wherein the plurality of tips are separated from each other at the pointed ends in the expanded position.

\* \* \* \* \*